(12) United States Patent
Hoshino et al.

(10) Patent No.: US 7,410,479 B2
(45) Date of Patent: Aug. 12, 2008

(54) DISPOSABLE ABSORBENT ARTICLE

(75) Inventors: Minoru Hoshino, Kiryu (JP); Fumiko Aoki, Sawa-gun (JP)

(73) Assignee: Hakujuji Kabushiki Kaisha, Tokyo (JP)

( * ) Notice: Subject to any disclaimer, the term of this patent is extended or adjusted under 35 U.S.C. 154(b) by 153 days.

(21) Appl. No.: 10/500,347

(22) PCT Filed: Aug. 22, 2003

(86) PCT No.: PCT/JP03/10625

§ 371 (c)(1),
(2), (4) Date: Jun. 25, 2004

(87) PCT Pub. No.: WO2004/017875

PCT Pub. Date: Mar. 4, 2004

(65) Prior Publication Data

US 2005/0096624 A1    May 5, 2005

(30) Foreign Application Priority Data

Aug. 23, 2002   (JP) .............................. 2002-244368

(51) Int. Cl.
*A61F 13/15* (2006.01)
*A61F 13/20* (2006.01)

(52) U.S. Cl. ............................ 604/385.27; 604/385.24; 604/385.25; 604/385.26; 604/385.29

(58) Field of Classification Search ............. 604/385.27
See application file for complete search history.

(56) References Cited

U.S. PATENT DOCUMENTS

| 5,899,894 | A | * | 5/1999 | Palumbo et al. ............. 604/378 |
| 6,179,820 | B1 | * | 1/2001 | Fernfors ................ 604/385.27 |
| 2003/0040732 | A1 | * | 2/2003 | Ishikawa et al. ........ 604/385.29 |

FOREIGN PATENT DOCUMENTS

JP        09-313531 A       12/1977

(Continued)

OTHER PUBLICATIONS

Dictionary entry from MSN Encarta Online for the word "along".*

(Continued)

*Primary Examiner*—T. Zalukaeva
*Assistant Examiner*—Melanie J Hand
(74) *Attorney, Agent, or Firm*—Cheryl F. Cohen, LLC

(57) ABSTRACT

An absorbent article body part includes a liquid permeable surface side sheet, a liquid impermeable back face side sheet, and an absorbent body, positioned between the sheets, and having flap parts, extending outward to the respective sides of the absorbent body, and is formed by layering an outer layer sheet onto the back face side of the main absorbent article body part. At the outer layer sheet, first and second leg part elastic bodies are positioned with sides at one end being set along leg parts from parts of a dorsal waist part at one side and the other side, intermediate parts crossing a crotch part obliquely, and the sides at the other end being set along the leg parts at parts of a ventral waist part at the other side and the one side. Third leg part elastic bodies are positioned along the longitudinal direction at the flap parts.

14 Claims, 9 Drawing Sheets

FOREIGN PATENT DOCUMENTS

| | | |
|---|---|---|
| JP | 06-296638 A | 10/1994 |
| JP | 08-84747 A | 4/1996 |
| JP | 09-313534 A | 12/1997 |
| JP | 09313531 A * | 12/1997 |
| JP | 11-146894 A | 6/1999 |
| JP | 11-155901 A | 6/1999 |
| JP | 11-290377 A | 10/1999 |
| JP | 2000-093462 | 4/2000 |
| JP | 2001-276120 A | 10/2001 |
| JP | 2002-85452 A | 3/2002 |
| JP | 2002-209942 | 7/2002 |
| JP | 2003-339750 | 12/2003 |

OTHER PUBLICATIONS

Dictionary entry from Cambridge Dictionaries Online for the word "along".*

Dictionary entry from The Wordsmyth English Dictionary Online for the word "along".*

* cited by examiner

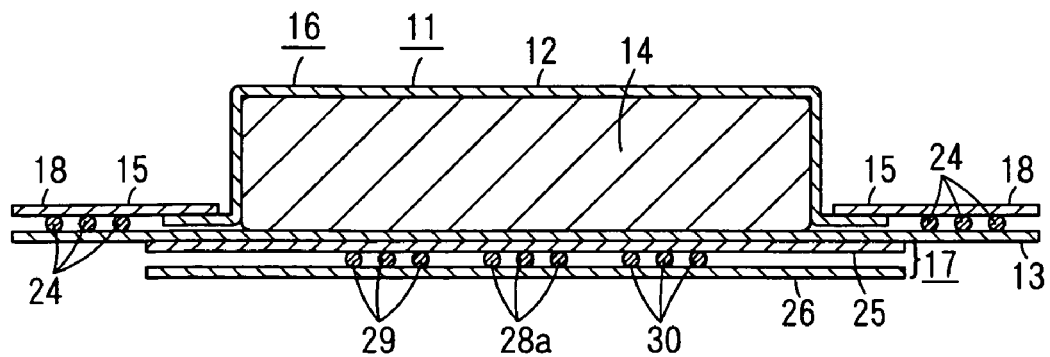
F I G. 2
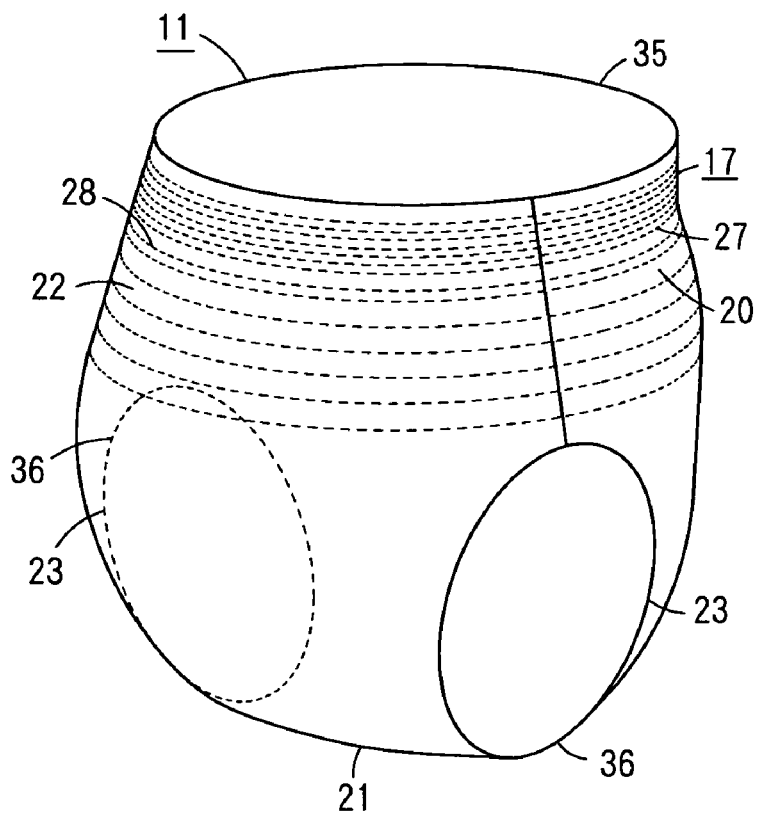
F I G. 3

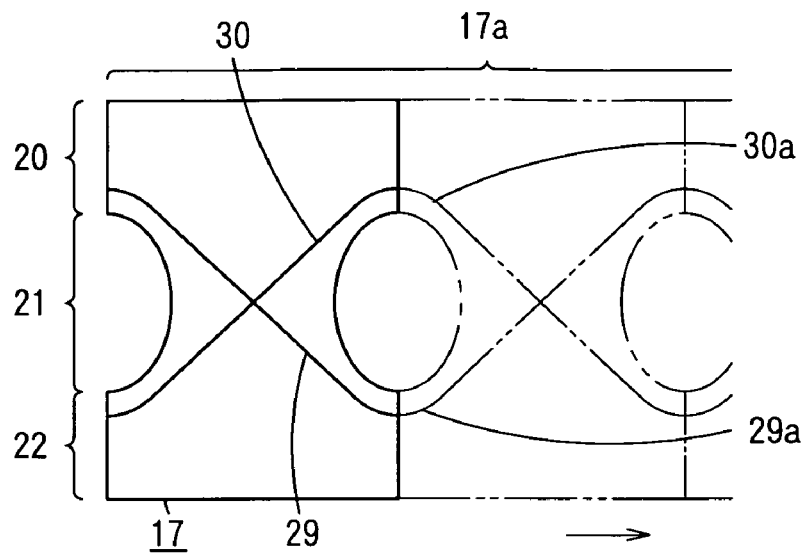
F I G. 4
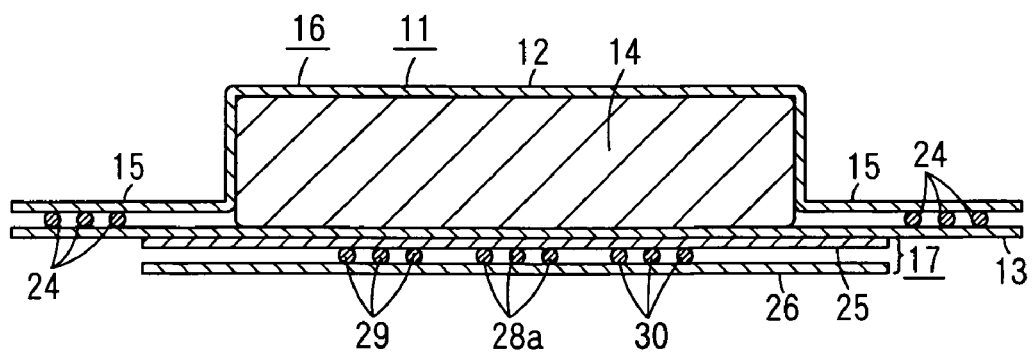
F I G. 5

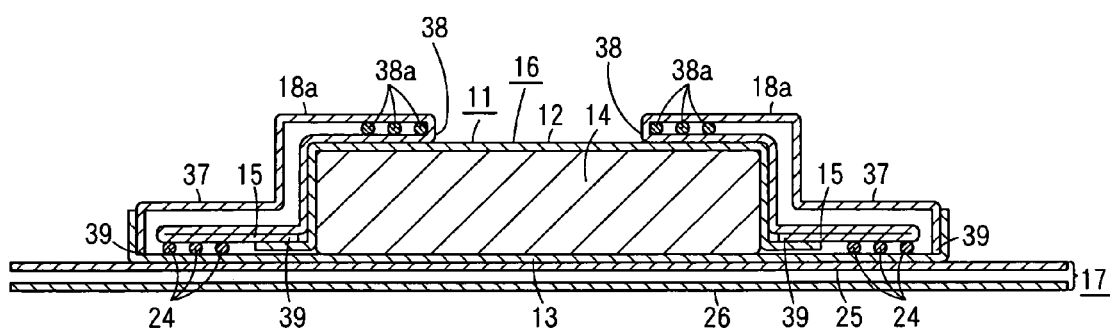
F I G. 7

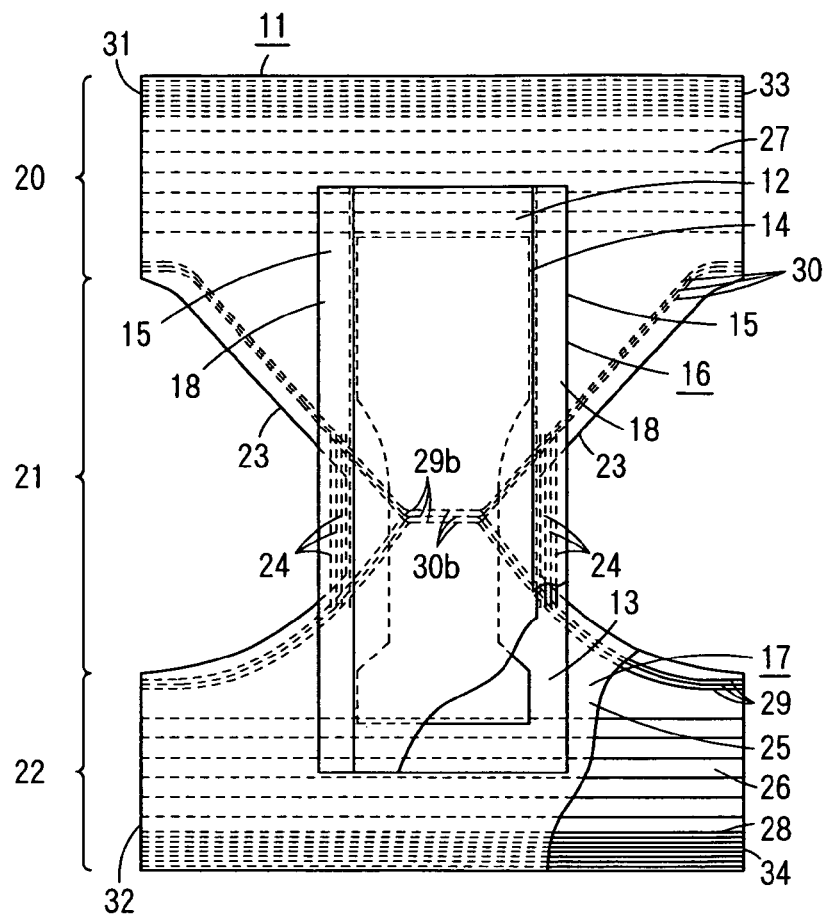
F I G. 1 1
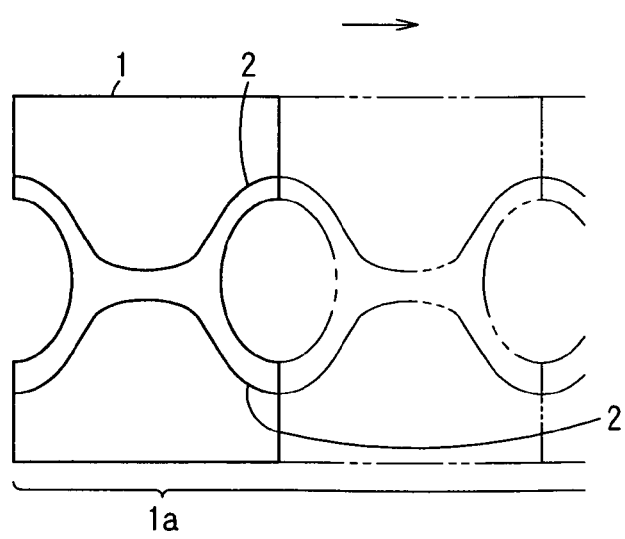
F I G. 1 2   PRIOR ART

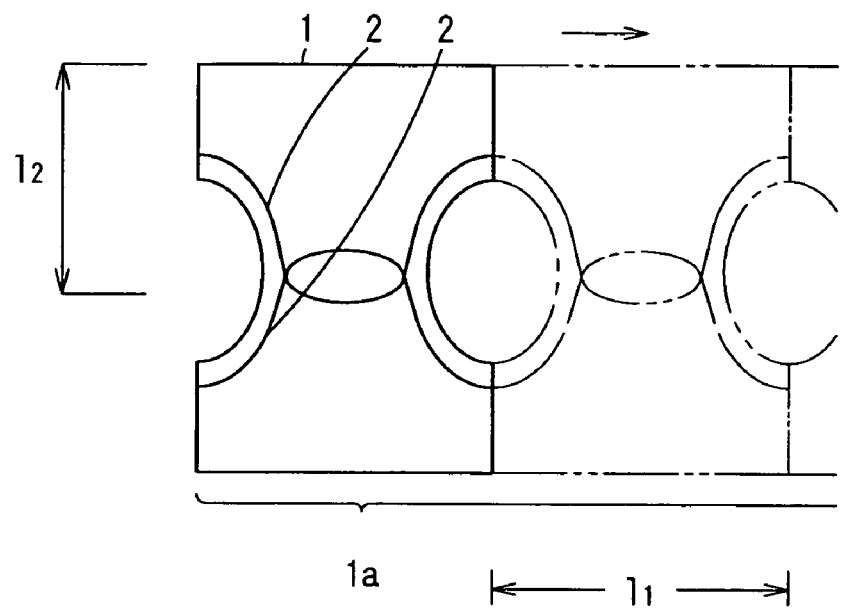
F I G. 1 3    PRIOR ART
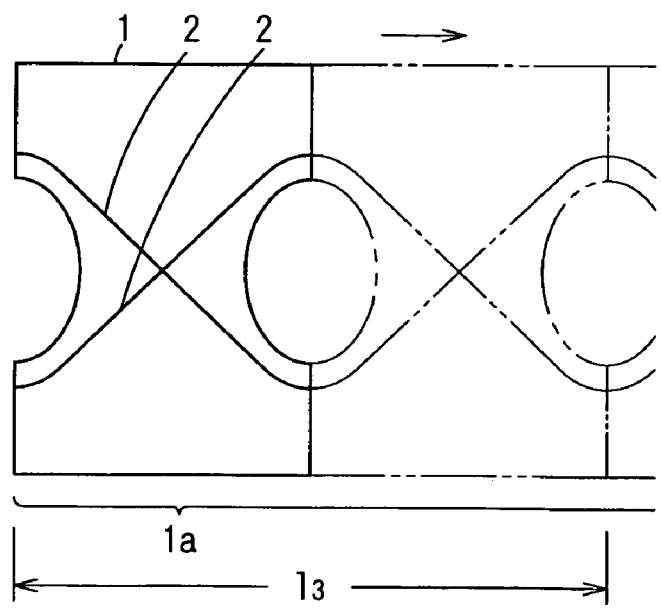
F I G. 1 4    PRIOR ART

DISPOSABLE ABSORBENT ARTICLE

CROSS-REFERENCE TO PRIOR APPLICATION

This is a U.S. national phase application under 35 U.S.C. §371 of International Patent Application No. PCT/JP2003/010625 filed Aug. 22, 2003, and claims the benefit of Japanese Patent Application No. 2002-244368 filed Aug. 23, 2002 which is incorporated by reference herein. The International Application was published in Japanese on Mar. 4, 2004 as WO 2004/017875 A1 under PCT Article 21(2).

TECHNICAL FIELD

This invention concerns a disposable absorbent article, such a disposable diaper for adult use or for incontinence, etc.

BACKGROUND ART

As the above-mentioned type of disposable diaper or other disposable absorbent article, a disposable absorbent article, with which a liquid permeable surface side sheet, an absorbent body, and a liquid impermeable back face side sheet are layered to form a dorsal waist part, a crotch part, and a ventral waist part successively and integrally in the longitudinal direction, has been known generally since priorly.

Also, a disposable diaper, with which an outer layer sheet, forming a dorsal waist part, a crotch part, and a ventral waist part integrally and successively in the longitudinal direction, is affixed to the back face side of a main absorbent article body part, arranged from a liquid permeable surface side sheet, an absorbent body, and a liquid impermeable back face side sheet, has been proposed (Japanese Patent Application No. 2002-158359). With the outer layer sheet of this disposable diaper, a dorsal waist part elastic body is positioned at the dorsal waist part, a ventral waist part elastic body is positioned at the ventral waist part, and leg part elastic bodies are positioned at parts of both legs.

Furthermore as shown in FIG. 12, with this disposable diaper, the respective end parts of leg part elastic bodies 2,2 are positioned along leg parts at the dorsal waist part side and leg parts at the ventral waist part side of outer layer sheet 1, and intermediate parts of these leg part elastic bodies 2,2 are positioned across the crotch part in a mutually separated and opposing manner. Also, leg part elastic bodies 2,2 are positioned in substantially U-like form so as to be substantially symmetrical at the dorsal part and the ventral part.

However, with this disposable diaper, the effects of stretching of leg part elastic bodies 2,2 are separated into that of the dorsal side at the dorsal side and that of the ventral side at the ventral side, and the effect of putting the entirety of the diaper body into close contact with the body of a wearer, especially at the crotch part, cannot be obtained readily.

Also, though the manufacturing properties are improved due to the movement distance of leg part elastic bodies 2,2 in the width direction of an outer layer sheet component material 1a being comparatively low, since leg part elastic bodies 2,2 are separated in an opposing manner in the longitudinal direction of the outer layer sheet at the crotch part and an elastic body is not positioned at a substantially central part in the longitudinal direction of the leg parts at both sides, this disposable diaper cannot be put readily in close contact with the body of a wearer across substantially the entireties of the leg parts at both sides and excreted fluids may leak while the disposable diaper is worn.

Thus an arrangement may be considered wherein leg part elastic bodies 2,2 are positioned along the leg parts at the respective sides of outer layer sheet 1 of a disposable diaper so that the leg part elastic bodies 2,2 that are provided at the leg parts at the respective sides will be positioned at the parts at which they are mutually separated in outer layer sheet 1, thereby providing substantially the entireties of the leg parts at both sides of the above-mentioned disposable diaper with stretchability.

As a method for manufacturing this type of disposable diaper, a method of moving a long outer layer sheet component material 1a, which is outer layer sheet 1 made continuous in the width direction, in its longitudinal direction (direction indicated by the arrow in FIG. 12) and meanwhile positioning waist part elastic bodies of long length (not illustrated) and leg part elastic bodies 2,2 of long length in a continuous manner in the longitudinal direction, and then cutting the above-mentioned outer layer sheet component material 1a in the width direction to form outer layer sheet 1, has been proposed (Japanese Patent Application No. 2002-158359).

In this process, the waist part elastic bodies are positioned in the form of straight lines while being stretched in the longitudinal direction of outer layer sheet component material 1a, and leg part elastic bodies 2,2 are positioned while being moved and stretched in the width direction of outer layer sheet component material 1a.

However, with each of the above-described arrangements, since leg part elastic bodies 2,2 are positioned along a direction that intersects the movement direction of outer layer sheet component material 1a, that is, along the width direction, leg part elastic bodies 2,2 must be stretched and positioned while being moved at a high speed in comparison to the movement speed of outer layer sheet component material 1a. The manufacturing process is therefore not easy.

An arrangement can thus be considered wherein leg part elastic bodies 2,2 are positioned on outer layer sheet 1 so that the respective end parts thereof are set along the leg parts at the dorsal part side and the ventral part side and positioned on outer layer sheet 1 so that the intermediate parts respectively intersect at the crotch part and cross the crotch part obliquely as shown in FIG. 13.

With the present disposable diaper, an outer layer sheet component material 1a of long length is moved in its longitudinal direction (direction indicated by the arrow in FIG. 13) as with the arrangement shown in FIG. 12 and at the same time, the respective leg part elastic bodies 2,2 are curved in a U-turning manner in the width direction at the central part in the width direction of the above-mentioned outer layer sheet component material 1a so as to intersect mutually at the intermediate parts. Leg part elastic bodies 2,2 are thereby positioned as a pair of opposing U-like forms that intersect in the longitudinal direction. Since leg part elastic bodies 2,2 are positioned across substantially the entireties of the leg parts at both sides of outer layer sheet 1, this disposable diaper can be put into close contact with the entirety of the crotch area of a wearer when it is worn.

However, since leg part elastic bodies 2,2 of this disposable diaper intersect and oppose each other in the longitudinal direction at the crotch part and the width direction dimension along which leg part elastic bodies 2,2 are positioned on the outer layer sheet component material 1a of long length in the manufacturing process thus becomes large in comparison to the arrangement shown in FIG. 12, the movement distances of leg part elastic bodies 2,2 in the width direction over the long outer layer sheet 1 become large and the manufacturing process is therefore not easy.

That is, in the case where leg part elastic bodies 2,2 are to be positioned in a manner in which they oppose each other in the longitudinal direction of outer layer sheet 1 and are mutually curved in a substantially U-like shape, the above-mentioned leg part elastic bodies 2,2 must be reciprocated across a curving width dimension $l_2$ while outer layer sheet component material 1a is moved across the length dimension $l_1$, corresponding to the width direction dimension for a single outer layer sheet 1 shown in FIG. 13. Thus in comparison to the arrangement shown in FIG. 12, the curving movement amounts of leg part elastic bodies 2,2 become large, the movement speed of a device for positioning leg part elastic bodies 2,2 becomes high, and leg part elastic bodies 2,2 therefore cannot be positioned readily on outer layer sheet component material 1a.

An arrangement can thus be considered wherein one of the above-mentioned leg part elastic bodies 2,2 is positioned so as to cross obliquely across the crotch part from a part of the dorsal waist part at one side to a part of the ventral waist part at the other side, the other leg part elastic body 2 is positioned so as to cross obliquely across the crotch part from a part of the above-mentioned dorsal waist part at the other side to a part of the above-mentioned ventral waist part at the one side, and the pair of leg part elastic bodies 2,2 are made to intersect mutually and form a substantially X-like shape at the crotch part as shown in FIG. 14.

With the disposable diaper shown in FIG. 14, when a single cycle is defined as the interval in the manufacturing process in which the above-mentioned outer layer sheet component material 1a is moved over a length dimension $l_3$, corresponding to the width direction dimension of two outer layer sheets 1, it is sufficient for a device for positioning leg part elastic bodies 2,2 to reciprocate across the width direction of the above-mentioned outer layer sheet component material 1a during this single cycle, and since the above-mentioned positioning device thus does not have to be moved at a high speed in the width direction of the above-mentioned outer layer sheet component material 1a in comparison to the arrangements shown in FIGS. 12 and 13, leg part elastic bodies 2,2 can be positioned comparatively readily.

However, when leg part elastic bodies 2,2 are intersected mutually in a substantially X-like manner at the crotch part of outer layer sheet 1, the leg part elastic bodies 2,2 positioned at substantially the central part of the above-mentioned crotch part of the above-mentioned outer layer sheet 1 cannot make the leg parts at the respective sides of the disposable diaper be stretched in the longitudinal direction of the disposable absorbent article. Thus when the above-mentioned disposable absorbent article is fitted onto the body of a wearer, excreted fluids may leak out from the leg parts at the respective sides of the disposable absorbent article.

This invention has been made in view of the above problems, and an object thereof is to provide an absorbent article, with which good close contact is realized at the leg parts at both sides when the article is fitted onto the body of a wearer, the function of preventing the leakage of excreted fluids is improved, and leg part elastic bodies can be positioned readily during manufacture so as to enable manufacture to be performed readily.

DISCLOSURE OF THE INVENTION

This invention's disposable absorbent article comprises: a main absorbent article body part, in turn comprising a liquid permeable surface side sheet, a liquid impermeable back face side sheet, positioned at the back face side of the liquid permeable surface side sheet, an absorbent body, positioned between the liquid permeable surface side sheet and the liquid impermeable back face side sheet, and flap parts, formed at least at the peripheral edge parts of the above-mentioned liquid impermeable back face side sheet and extending outward beyond the respective sides in the width direction of the above-mentioned absorbent body; and an outer layer sheet, positioned at the back face side of the liquid impermeable back face side sheet of the main absorbent article body part; and is characterized in that a dorsal waist part, a crotch part, having leg parts at both sides, and a ventral waist part are formed successively and integrally in the longitudinal direction, a dorsal waist part elastic body and a ventral waist part elastic body, which stretch in the width direction of the outer layer sheet, are disposed respectively at the dorsal waist part and the ventral waist part of the above-mentioned outer layer sheet, leg part elastic bodies are disposed respectively at the above-mentioned leg parts at the respective sides of the above-mentioned outer layer sheet, the above-mentioned leg part elastic bodies are formed as first leg part elastic bodies and second leg part elastic bodies, the first leg part elastic bodies have one end side set along a leg part from a part of the above-mentioned dorsal waist part at one side, have an intermediate part crossing the above-mentioned crotch part obliquely towards a part of the above-mentioned ventral waist part at the other side, and have the other end side set along the leg part at the part of the above-mentioned ventral waist part at the other side, the second leg part elastic bodies have one end side set along a leg part from a part of the above-mentioned dorsal waist part at the other side, have an intermediate part intersecting the above-mentioned first leg part elastic bodies and crossing the above-mentioned crotch part obliquely towards a part of the above-mentioned ventral waist part at the one side, and have the other end side set along the leg part at the part of the ventral waist part side at the above-mentioned one side, and third leg part elastic bodies are disposed along the flap parts at both sides of the above-mentioned main absorbent article body part. And by the first leg part elastic bodies having one end side set along a leg part from a part of the above-mentioned dorsal waist part at one side, the intermediate part crossing the above-mentioned crotch part obliquely towards a part of the above-mentioned ventral waist part at the other side, and the other end side set along the leg part at the part of the above-mentioned ventral waist part at the other side, the second leg part elastic bodies having one end side set along a leg part from a part of the above-mentioned dorsal waist part at the other side, the intermediate part intersecting the above-mentioned first leg part elastic bodies and crossing the above-mentioned crotch part obliquely towards a part of the above-mentioned ventral waist part at the one side, and the other end side set along the leg part at the part of the ventral waist part side at the above-mentioned one side, and the third leg part elastic bodies being disposed along the flap parts at both sides of the above-mentioned main absorbent article body part, leg part elastic bodies are disposed over substantially the entireties of the leg parts of the disposable absorbent article so that substantially the entireties of the leg parts are put in close contact with the leg parts of a wearer and the function of preventing the leakage of excreted fluids from the leg parts of the main absorbent article body part is improved.

Also in regard to the positioning of the first leg part elastic bodies and the second leg part elastic bodies on a long outer layer sheet component material, which is continuous in the width direction, in manufacturing the outer layer sheet from the outer layer sheet component material, when a single cycle is defined as the time it takes for the outer layer sheet component material, corresponding to the width direction dimension for two disposable absorbent articles, to move across the positions at which the above-mentioned first and second leg part elastic bodies are to be positioned, it is sufficient that a device for positioning the above-mentioned first and second leg part elastic bodies be reciprocated along the width direction of the above-mentioned outer layer sheet component material within the single cycle, and since there is thus no need to move the above-mentioned positioning device at a high speed along the width direction of the above-mentioned outer layer sheet component material, the first leg part elastic bodies and the second leg part elastic bodies can be positioned readily. This disposable absorbent article can thus be manufactured readily without placing an excessive burden on a device for manufacturing the disposable absorbent article.

Furthermore in the manufacturing process, the main absorbent article body part can be formed integrally from a long component material in which the liquid permeable surface side sheet, the liquid impermeable back face side sheet, the flap parts at both sides, etc. are made continuous in the longitudinal direction, and with this long component material, long leg part elastic bodies that form the third leg part elastic bodies, positioned along the above-mentioned flap parts at both sides of the long component material, can be positioned along the movement direction of the above-mentioned long component material and these third leg part elastic bodies can thus be positioned readily on the above-mentioned main absorbent article body part.

Also this invention's disposable absorbent article comprises: a main absorbent article body part, in turn comprising a liquid permeable surface side sheet, a liquid impermeable back face side sheet, positioned at the back face side of the liquid permeable surface side sheet, an absorbent body, positioned between the liquid permeable surface side sheet and the liquid impermeable back face side sheet, and flap parts, formed at least at the peripheral edge parts of the above-mentioned liquid impermeable back face side sheet and extending outward beyond the respective sides in the width direction of the above-mentioned absorbent body; and an outer layer sheet, positioned at the side of the main absorbent article body part at the back face side of the liquid impermeable back face side sheet; and is characterized in that a dorsal waist part, a crotch part, having leg parts at both sides, and a ventral waist part are formed successively and integrally in the longitudinal direction, a dorsal waist part elastic body and a ventral waist part elastic body, which stretch in the width direction of the outer layer sheet, are disposed respectively at the dorsal waist part and the ventral waist part of the above-mentioned outer layer sheet, leg part elastic bodies are disposed respectively at the above-mentioned leg parts at the respective sides of the above-mentioned outer layer sheet, the above-mentioned leg part elastic bodies are formed as first leg part elastic bodies and second leg part elastic bodies, the first leg part elastic bodies have one end side set along a leg part from a part of the dorsal waist part at one side, have an intermediate part crossing the crotch part along the width direction, and have the other end side set along the leg part at a part of the ventral waist part at the other side, the second leg part elastic bodies have one end side set along a leg part from a part of the above-mentioned dorsal waist part at the other side, have an intermediate part substantially matched with the intermediate part of the above-mentioned first leg part elastic bodies and crossing the above-mentioned crotch part along the width direction, and have the other end side set along the leg part at a part of the ventral waist part side at the above-mentioned one side, and third leg part elastic bodies are disposed along the flap parts at both sides of the above-mentioned main absorbent article body part. And by the first leg part elastic bodies having one end side set along a leg part from a part of the above-mentioned dorsal waist part at one side, the intermediate part crossing the above-mentioned crotch part in the width direction, and the other end side set along the leg part at a part of the ventral waist part at the other side and the second leg part elastic bodies having one end side set along a leg part from a part of the above-mentioned dorsal waist part at the other side, the intermediate part substantially matched with the intermediate part of the above-mentioned first leg part elastic bodies and crossing the above-mentioned crotch part along the width direction, and the other end side set along the leg part at a part of the ventral waist part side at the above-mentioned one side, the first and second leg part elastic bodies can be positioned close to the respective leg parts, enabling the respective leg parts to be set readily along the leg parts of a wearer as well as enabling the respective leg part elastic bodies to be positioned so as to surround substantially the entireties of the leg parts at both sides even when the third leg part elastic bodies, which are disposed along the flap parts at both sides of the main absorbent article body part, are made short in length. Substantially the entireties of the leg parts are thus put in close contact with the leg parts of a wearer and the function of preventing the leakage of excreted fluids from the leg parts of the main absorbent article body part is improved.

Also in regard to the positioning of the first leg part elastic bodies and the second leg part elastic bodies on a long outer layer sheet component material, which is continuous in the width direction, in manufacturing the outer layer sheet from the outer layer sheet component material, when a single cycle is defined as the time it takes for the outer layer sheet component material, corresponding to the width direction dimension for two disposable absorbent articles, to move across the positions at which the above-mentioned first and second leg part elastic bodies are to be positioned, it is sufficient that a device for positioning the above-mentioned first and second leg part elastic bodies be reciprocated along the width direction of the above-mentioned outer layer sheet component material within the single cycle, and since there is thus no need to move the above-mentioned positioning device at a high speed along the width direction of the above-mentioned outer layer sheet component material, the first leg part elastic bodies and the second leg part elastic bodies can be positioned readily. This disposable absorbent article can thus be manufactured readily without placing an excessive burden on a device for manufacturing the disposable absorbent article.

Furthermore in the manufacturing process, the main absorbent article body part can be formed integrally from a long component material in which the liquid permeable surface side sheet, the liquid impermeable back face side sheet, the flap parts at both sides, etc. are made continuous in the longitudinal direction, and with this long component material, long leg part elastic bodies that form the third leg part elastic bodies, positioned along the above-mentioned flap parts at both sides of the long component material, can be positioned along the movement direction of the above-mentioned long component material and these third leg part elastic bodies can thus be positioned readily on the above-mentioned main absorbent article body part.

Also, with this invention's disposable absorbent article, the main absorbent article body part is affixed to the outer layer sheet at the back face side, the crotch part of the outer layer sheet is notched so as to be substantially concave towards the inner sides in the width direction, and the third leg part elastic bodies, which are positioned at the flap parts of the above-mentioned main absorbent article body part, have at least a portion thereof disposed outward beyond the leg parts at the respective sides of the outer layer sheet. By these third leg part elastic bodies, the parts of the main absorbent article body part that are positioned outward beyond the leg parts at both sides of the outer layer sheet stretch without being affected by the thickness or hardness of the outer layer sheet, and since the flap parts are thus put in close contact with the body of a wearer while the disposable absorbent article is worn, the function of preventing the leakage of excreted fluids from the leg parts is improved further.

Furthermore with this invention's disposable absorbent article, the third leg part elastic bodies are positioned at least respectively between the vicinities of the positions at which the first leg part elastic bodies and the outer side parts of the flap parts at the respective sides of the main absorbent article body part intersect and the vicinities of the positions at which the second leg part elastic bodies and the outer side parts of the flap parts at the respective sides of the main absorbent article body part intersect. The stretchability is thus secured over substantially the entireties of the leg parts at both sides of the disposable absorbent article while it is worn, close contact with the leg parts of a wearer is secured, and since only the third leg part elastic bodies, which are necessary for securing stretchability across substantially the entirety of the above-mentioned crotch part, need to be positioned, the use of elastic material can be reduced to lower the manufacturing cost of the disposable absorbent article.

Also with this invention's disposable absorbent article, a pair of three-dimensional gathers, which are erected in the direction of the body of a wearer when the absorbent article body is fitted onto the body of the wearer, are formed in mutually opposing manner at outer side parts at the respective sides that are positioned outward in the width direction beyond the vicinities of the third leg part elastic bodies of the main absorbent article body part. By the three-dimensional gathers being erected in the direction of the body of the wearer, the disposable absorbent article is put securely in close contact with the body of the wearer and the function of preventing the leakage of excreted fluids from the leg parts is improved further.

Furthermore with this invention's disposable absorbent article, each of the first leg part elastic bodies and second leg part elastic bodies is arranged to be lower in tensile strength at the intermediate part, positioned in the direction of crossing the above-mentioned crotch part, than at the one end side and the other end side that are positioned along the leg parts at the respective sides. The crotch part of the main absorbent article body part will therefore not be shrunken and narrowed more than necessary in the width direction and the disposable absorbent article can be fitted with close contact being secured with respect to the body of a wearer.

Also with this invention's disposable absorbent article, the outer layer sheet has central elastic bodies positioned along the longitudinal direction of the absorbent body at the width direction center of the absorbent body that is positioned at the surface side of the outer layer sheet. By the central elastic bodies being positioned at the width direction center of a pair of absorbent bodies, the absorbent bodies are made stretchable in the longitudinal direction and the absorbent article can be put in close contact more securely.

BRIEF DESCRIPTION OF THE DRAWINGS

FIG. 2 is a front longitudinal section of the disposable absorbent article along line A-A of FIG. 1, FIG. 3 is a perspective view of the pants form of the disposable absorbent article, FIG. 4 is a plan view of a state of manufacture of an outer layer sheet of the disposable absorbent article, FIG. 5 is front longitudinal section of a disposable absorbent article of another embodiment of this invention, FIG. 7 is a front longitudinal section of the disposable absorbent article along line B-B of FIG. 6, FIG. 11 is a partially cutaway plan view of a state in which a disposable absorbent article of another embodiment of this invention is spread out, FIG. 12 is an explanatory plan view of a state in which leg part elastic bodies of long length are positioned on an outer layer sheet component material of long length in the process of manufacturing an outer layer sheet of a priorly proposed disposable absorbent article, FIG. 13 is an explanatory plan view of a state in which leg part elastic bodies of long length are positioned on an outer layer sheet component material of long length in the process of manufacturing an outer layer sheet of a priorly proposed disposable absorbent article, and FIG. 14 is an explanatory plan view of a state in which leg part elastic bodies of long length are positioned on an outer layer sheet component material of long length in the process of manufacturing an outer layer sheet of a priorly proposed disposable absorbent article.

BEST MODE FOR CARRYING OUT THE INVENTION

An embodiment of this invention shall now be described with reference to the drawings.

A disposable absorbent article is equipped with an absorbent article body, for example, a diaper body 11 for adult use or for incontinence, etc.

Figure 1:
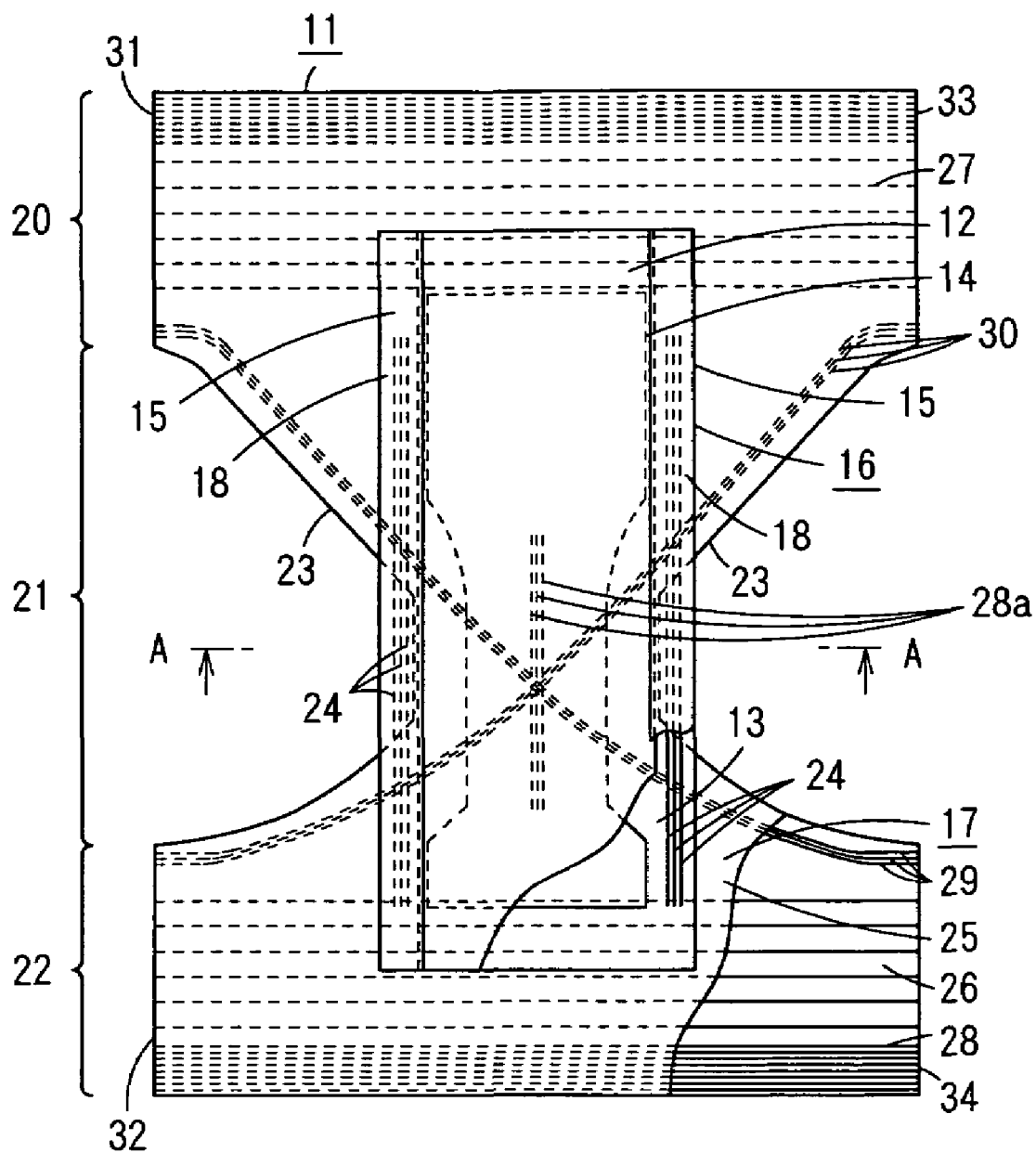
FIG. 1 is a partially cutaway plan view of a state in which a disposable absorbent article of an embodiment of this invention is spread out.

As shown in FIG. 1 and FIG. 2, this diaper body 11 is equipped with a main absorbent article body part 16, having a liquid permeable surface side sheet 12, a liquid impermeable back face side sheet 13, positioned at the back face side of liquid permeable surface side sheet 12, and an absorbent body 14, positioned between liquid permeable surface side sheet 12 and liquid impermeable back face side sheet 13, and on this main absorbent article body part 16 are formed flap parts 15, which extend outward beyond the respective end parts in the longitudinal direction and the respective side parts in the width direction of the above-mentioned absorbent body 14. Also, an outer layer sheet 17 is affixed to the back face side of the above-mentioned main absorbent article body part 16.

Furthermore, the above-mentioned liquid permeable surface side sheet 12 is formed of sheet material with liquid permeability and air permeability, such as woven cloth, non-woven cloth, porous film, synthetic fiber, etc., which is close in sensation to underwear, and allows the permeation of urine and other excreted fluids. This liquid permeable surface side sheet 12 is formed to a substantially slender, rectangular shape.

Liquid impermeable back face side sheet 13, which is layered onto the back face side of the above-mentioned liquid permeable surface side sheet 12, is formed of a sheet material of polyethylene resin or other synthetic resin, which is liquid impermeable, that is, impermeable to liquids and is air permeable, in order to prevent the soiling of underwear and other clothes or sheets, etc. by urine and other excreted fluids. This liquid impermeable back face side sheet 13 is formed to a substantially slender, rectangular shape and is formed to a size that is substantially the same as that of the above-abovementioned liquid permeable surface side sheet 12.

The above-mentioned absorbent body 14 is formed of material, having pulp for example as the main component and containing in part a substance, such as a polymer absorbent body, in order to adequately absorb urine and other excreted fluids and is formed to a sheet form by a pressing process. This absorbent body 14 is formed to a substantially slender, rectangular form with which the edges at both sides are notched so as to be substantially concave towards the inner side at substantially the middle part in the longitudinal direction, is smaller than the above-mentioned liquid permeable surface side sheet 12 and the above-mentioned liquid impermeable back face side sheet 13 in the longitudinal direction and width direction dimensions, and is positioned at substantially the center of the above-mentioned liquid permeable surface side sheet 12 and the above-mentioned liquid impermeable back face side sheet 13. The peripheral edge parts of the above-mentioned liquid permeable surface side sheet 12 are bonded to liquid impermeable back face side sheet 13 at parts outside the peripheral edge parts of the above-mentioned absorbent body 14, and the above-mentioned absorbent body 14 is sealed between the peripheral edge parts of the above-mentioned liquid permeable surface side sheet 12 and the above-mentioned liquid impermeable back face side sheet 13.

The above-mentioned flap parts 15 are formed by liquid impermeable sheets 18, which are layered and adhesively bonded to parts of the above-mentioned liquid permeable surface side sheet 12 and the above-mentioned liquid impermeable back face side sheet 13 that extend beyond the peripheral edges of the above-mentioned absorbent body 14 and parts at both sides in the width direction of the surface side of the above-mentioned liquid permeable surface side sheet 12 and the above-mentioned liquid impermeable back face side sheet 13, and are formed so as to extend outward beyond the respective end parts in the longitudinal direction and the respective side parts in the width direction of the above-mentioned absorbent body 14.

The above-mentioned outer layer sheet 17 is formed by overlapping and integrally bonding an inner sheet piece 25, having air permeability and liquid impermeability, and an outer sheet piece 26, having liquid impermeability. In the spread-out state, this outer layer sheet 17 has a dorsal waist part 20, crotch part 21, and a ventral waist part 22 formed successively and integrally in the longitudinal direction of diaper body 11 and is formed to a rectangular shape that is substantially line symmetrical with respect to the central line along the longitudinal direction. Parts at both sides of crotch part 21 of this outer layer sheet 17 are notched to be substantially concave towards the inner width direction, thereby forming leg parts 23.

Furthermore, dorsal waist part 20 and ventral waist part 22 of outer layer sheet 17 are formed to substantially rectangular shapes with which the width direction dimension is longer than the longitudinal direction dimension. At dorsal waist part 20 and ventral waist part 22, a dorsal waist part elastic body 27 and ventral waist part elastic body 28, each formed of a plurality of cord-like elastic members, are respectively affixed in the width direction in stretched states between inner sheet piece 25 and outer sheet piece 26.

At crotch part 21 of the above-mentioned outer layer 17, central elastic bodies 28a are positioned and affixed between the above-mentioned inner sheet piece 25 and outer sheet piece 26 at the width direction center of absorbent body 14 in a state in which they are stretched along the longitudinal direction of diaper body 11. These central elastic bodies 28a are formed of several elastic bodies that are in turn formed of thin rubber cords, etc. and stretch in the longitudinal direction of the above-mentioned outer layer sheet 17.

At the above-mentioned leg parts 23 of the respective sides of the above-mentioned outer layer sheet 17 are positioned first leg part elastic bodies 29 and second leg part elastic bodies 30.

Between inner side sheet 25 and outer side sheet 26 of the above-mentioned outer layer sheet 17, first leg part elastic bodies 29 have one end side set along a leg part 23 from a part of dorsal waist part 20 at one side, have an intermediate part obliquely crossing the above-mentioned crotch part 21 towards a part of the above-mentioned ventral waist part 22 at the other side, and have the other end side set along the leg part 23 at the part of ventral waist part 22 at the above-mentioned other side.

Also, second leg part elastic bodies 30 have one end side set along a leg part 23 from a part of dorsal waist part 20 at the above-mentioned other side, have an intermediate part intersecting the above-mentioned first leg part elastic bodies 29 in an X-like form and obliquely crossing the above-mentioned crotch part 21 towards a part of ventral waist part 22 at the above-mentioned one side, and have the side at the other end set along the leg part 23 at the part of the ventral waist part 22 at the above-mentioned one side.

These first leg part elastic bodies 29 and second leg part elastic bodies 30 are positioned in stretched states such that the intermediate parts that are positioned in directions of crossing the above-mentioned crotch part 21 are less in tensile strength than the one end side and the other end side that are positioned along leg parts 23 at the respective sides.

That is, the respective elastic bodies 29 and 30 are positioned so that the vicinities of the intersections of these elastic bodies 29 and 30, which are parts that are not set along the vicinities of the respective edges of leg parts 23, will be lower in tensile strength than the respective end parts of these elastic bodies 29 and 30.

Also, third leg part elastic bodies 24 are respectively positioned at flap parts 15 at the respective sides of the above-mentioned main absorbent article body part 16. These third leg part elastic bodies 24 are each formed of several thin cords of rubber, etc. and are affixed in stretched states across substantially the entirety of the respective longitudinal direction side parts of the above-mentioned absorbent body 14 and between liquid impermeable sheets 18 and the respective side parts of the above-mentioned liquid impermeable back face side sheet 13. Also, at leg parts 23 of the above-mentioned outer layer sheet 17, third leg part elastic bodies 24 are positioned outward beyond leg parts 23 at the respective sides of the above-mentioned outer layer sheet 17.

The above-mentioned first leg part elastic bodies 29 and second leg part elastic bodies 30 intersect third leg part elastic bodies 24 in the same plane at the vicinities of the positions at which the above-mentioned flap parts 15, which are outer side parts of main absorbent article body part 16, intersect with the above-mentioned first leg part elastic bodies 29.

Also, central elastic bodies 28a intersect elastic bodies 29 and 30 at the part at which elastic bodies 29 and 30 intersect each other.

This diaper body 11 is formed to a pants form, having a waist side opening 35, which opens upwards, and a pair of leg side openings 36, which open downwards, in the state in which an outer edge part 31 at one side of dorsal waist part 20 of outer layer sheet 17 is bonded by an adhesive agent, etc. to an outer edge part 32 at one side of ventral waist part 22 and an outer edge part 33 at the other side of dorsal waist part 20 is bonded by an adhesive agent, etc. to an outer edge part 34 at the other side of ventral waist part 22 so that the liquid permeable surface side sheet 12 of the diaper body 11 may be the inner surface side of the diaper body 11, as shown in FIG. 3.

The actions of this embodiment shall now be described.

First in the process of manufacturing diaper body 11, a long outer layer sheet component material 17a, which is the above-mentioned outer sheet 17 made continuous, is moved in the longitudinal direction as shown in FIG. 4 and in the meantime, waist part elastic bodies of long length (not shown) are affixed continuously in the longitudinal direction.

Next, on the above-mentioned outer layer sheet component material 17a, the above-mentioned first leg part elastic bodies 29 are positioned with one end side set along a leg part 23 from a part of dorsal waist part 20 at one side, an intermediate part crossing the above-mentioned crotch part 21 obliquely towards a part of the above-mentioned ventral waist part 22 at the other side, and the other end side set along the leg part 23 at the part of ventral waist part 22 at the above-mentioned other side. The above-mentioned second leg part elastic bodies 30 are positioned with one end side set along a leg part 23 from a part of dorsal waist part 20 at the above-mentioned other side, an intermediate part crossing the above-mentioned crotch part 21 obliquely towards a part of ventral waist part 22 at the above-mentioned one side, and the other end side set along the leg part 23 at the part of ventral waist part 22 at the above-mentioned one side.

Furthermore, outer layer sheet component material 17a is cut in the width direction at the part at which first leg part elastic bodies 29a of long length and second leg part elastic bodies 30a of long length are separated the most, thereby forming outer layer sheet 17.

In regard to the positioning of the long first leg part elastic bodies 29a and the long second leg part elastic bodies 30a on the above-mentioned outer layer sheet component material 17a while moving the long outer layer sheet component material 17a in the longitudinal direction in the process of manufacturing diaper body 11, when a single cycle is defined as the time in which outer sheet layer component material 17a, corresponding to the width direction dimension of two of the above-mentioned diaper bodies 11, passes across the positions at which the above-mentioned first leg part elastic bodies 29 and second leg part elastic bodies 30 are positioned, a device for positioning the above-mentioned first leg part elastic bodies 29 and a device for positioning the above-mentioned second leg part elastic bodies 30 are reciprocated across the width direction of the above-mentioned outer layer sheet component material 17a during this single cycle. Since the above-mentioned positioning devices thus do not have to be moved at a high speed in the width direction of the above-mentioned outer layer sheet component material 17a, the above-mentioned first leg part elastic bodies 29 and second leg part elastic bodies 30 can be positioned readily.

Furthermore in the manufacturing process, main absorbent article body part 16 can be formed integrally from a component material of long length in which liquid permeable surface side sheet 12, liquid impermeable back face side sheet 13, flap parts 15 at both sides, etc. are made continuous in the longitudinal direction, and with this long component material, leg part elastic bodies of long length that form third leg part elastic bodies 24, which are positioned along the above-mentioned flap parts 15 at both sides of the long component material, can be positioned along the movement direction of the above-mentioned long component material and these third leg part elastic bodies 24 can thus be positioned readily on the above-mentioned main absorbent article body part 16.

In being fitted on, diaper body 11 can be fitted on readily like pants.

In regard to the above-mentioned first leg part elastic bodies 29, the above-mentioned second leg part elastic bodies 30, and the above-mentioned third leg part elastic bodies 24, which are positioned along flap parts 15 at both sides of main absorbent article body part 16, since the above-mentioned first leg part elastic bodies 29, second leg part elastic bodies 30, and third leg part elastic bodies 24 are positioned so as to surround substantially the entireties of leg parts 23 of diaper body 11, substantially the entireties of leg parts 23 of diaper body 11 are put securely in close contact with the leg parts of a wearer.

Also, since flap parts 15 of main absorbent article body part 16 are positioned at the outer side of leg parts 23 at both sides of outer layer sheet 17, at least parts of third leg part elastic bodies 24, which are positioned at flap parts 15, that is, at the parts positioned at the part of the narrowest crotch width at which outer layer sheet 17 is notched in concave form, are positioned at the outer side of leg parts 23 at both sides of outer layer sheet 17. Thus at least the parts of main absorbent article body part 16 and third leg part elastic bodies 24 that are positioned at the outer side of leg parts 23 at both sides of outer layer sheet 17 provide a good stretching action without being hindered by the thickness or hardness of outer layer sheet 17 and, while the diaper is worn, are securely put in close contact with the leg parts of a wearer in a manner such as if outer layer sheet 17 itself is stretching.

Furthermore, since the above-mentioned central elastic bodies 28a are positioned in a state in which they are stretched along the longitudinal direction of diaper body 11 at the width direction center of the above-mentioned absorbent body 14, which is positioned at the surface side of the above-mentioned outer layer sheet 17 and since the above-mentioned absorbent body 14 can thus be stretched in the longitudinal direction of the above-mentioned outer layer sheet 17 and pushed upwards in the direction of the body of a wearer by the shrinking of these central elastic bodies 28a, diaper body 11 can be put securely in close contact with the body of the wearer and the function of preventing the leakage of excreted fluids can be improved further.

Also by making small the tensile strengths of the intermediate parts of first leg part elastic bodies 29 and second leg part elastic bodies 30, which are positioned in the direction of crossing the above-mentioned crotch part 21, crotch part 21 of the above-mentioned diaper body 11 is prevented from shrinking more than necessary in the width direction so that the crotch portion of diaper body 11 is prevented from becoming narrower than necessary and the above-mentioned diaper body 11 is thus fitted with close contact being secured with respect to the body of a wearer.

Also with flap parts 15 of main absorbent article body part 16, since by the layering and adhesive bonding of liquid impermeable sheets 18 onto the peripheral edge parts at the surface side of liquid permeable surface side sheet 12, the above-mentioned flap parts 15 are arranged to be liquid impermeable at the side of the skin of a wearer when the above-mentioned diaper body 11 is worn, the function of preventing the leakage of excreted fluids from the above-mentioned crotch part 21 can be improved.

Though with this embodiment, the wearer body sides of flap parts 15 of the above-mentioned main absorbent article body part 16 are formed by the layering of liquid impermeable sheets 18 onto the peripheral edge parts at the surface side of liquid impermeable back face side sheet 13, in place of using these liquid impermeable sheets 18, the longitudinal direction and width direction dimensions of the above-mentioned liquid permeable surface side sheet 12 may be formed to be substantially the same as those of the above-mentioned liquid impermeable back face side sheet 13 and the peripheral edge parts of this liquid permeable surface side sheet 12 may be layered and bonded onto the peripheral edge parts of the above-mentioned liquid impermeable back face side sheets 13 to form flap parts as shown in FIG. 5.

By thus forming a part of flap parts 15 of the above-mentioned main absorbent article body part 16 from the peripheral edge parts of the above-mentioned liquid permeable surface side sheet 12, the number of component members that form the above-mentioned main absorbent article body part 16 can be lessened, thus enabling this main absorbent article body part 16 to be manufactured in fewer steps to enable the manufacturing property to be improved, and furthermore since there is no need to use liquid impermeable sheets 18, the manufacturing cost can be restrained further.

Figure 6:
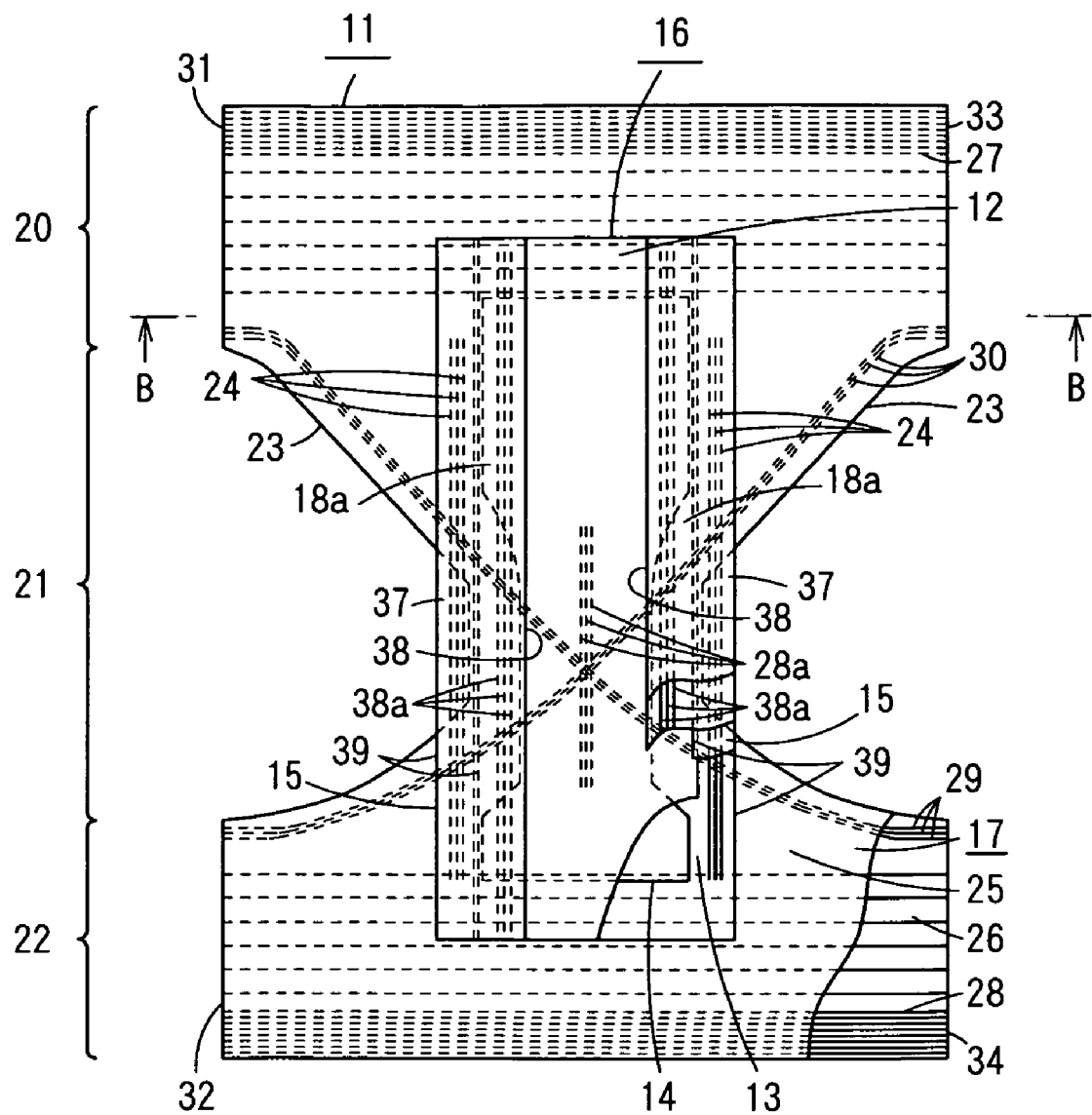
FIG. 6 is a partially cutaway plan view of a state in which a disposable absorbent article of another embodiment of this invention is spread out.

The arrangement of another embodiment of this invention's disposable absorbent article shall now be described with reference to FIG. 6 and FIG. 7. With regard to arrangements and actions that are the same as those of the embodiments described above, the same symbols shall be attached and description thereof shall be omitted.

A diaper body 11 has three-dimensional gathers 37 at the respective outer side parts that positioned outward in the width direction beyond the respective width direction side parts of flap parts 15.

The above-mentioned flap parts 15 are formed from parts of a liquid permeable surface side sheet 12 and a liquid impermeable back face side sheet 13 extending outward beyond the peripheral edges of absorbent body 14 and from three-dimensional gather sheets 18*a*, formed of liquid impermeable sheets and layered and adhesively bonded to the above-mentioned liquid permeable surface side sheet 12 and the respective width direction side parts at the surface sides of the above-mentioned liquid impermeable back face side sheet 13, and extend outward beyond the respective end parts in the longitudinal direction and the respective side parts in the width direction of the above-mentioned absorbent member 14. At flap parts 15, third leg part elastic bodies 24, each formed of a plurality of thin cords of rubber, etc., are positioned between the respective side parts of the above-mentioned liquid impermeable back face side sheet 13 and three-dimensional gather sheets 18*a* across substantially the entireties of the respective side parts in the longitudinal direction of the above-mentioned absorbent body 14.

The above-mentioned three-dimensional gather sheets 18*a*,18*a* are folded in two, base end parts 39 at one side of these three-dimensional gather sheets 18*a*,18*a* are affixed and bonded by an adhesive agent, etc. to the vicinities of the respective width direction side parts of the above-mentioned liquid permeable surface side sheet 12, and base end parts 39 at the other side are affixed and bonded by an adhesive agent, etc. to the vicinities of the respective width direction side parts of the above-mentioned liquid impermeable back face side sheet 13 to form three-dimensional gathers 37,37. Also the mutually opposing inner side parts of the respective longitudinal direction end parts of three-dimensional gather sheets 18*a*,18*a* are overlapped with and adhered and bonded to the upper surface of the above-mentioned liquid permeable surface side sheet 12.

Three-dimensional gather forming elastic bodies 38*a* are sandwiched and affixed in stretched states in the above-mentioned three-dimensional gather sheets 18*a*, 18*a* at the vicinities of front end parts 38 at which three-dimensional gather sheets 18*a*,18*a*, which form the above-mentioned three-dimensional gathers 37,37, are folded. These three-dimensional gather forming elastic bodies 38*a* are each formed of plurality of thin cords of rubber, etc. and are positioned across substantially the entireties of the respective longitudinal direction sides of the above-mentioned three-dimensional gathers 37.

The actions of this embodiment shall now be described.

In being fitted on, diaper body 11 is fitted on readily like pants as with the respective embodiments described above.

When diaper body 11 is fitted onto the body of a wearer, the above-mentioned three-dimensional gather forming elastic bodies 38*a* shrink, thereby erecting three-dimensional gathers 37 towards the inner side of diaper body 11, that is, in the direction of the body of the wearer. Diaper body 11 is thus put securely in close contact with the body of the wearer.

Also by forming the above-mentioned three-dimensional gathers 37 from three-dimensional gather sheets 18*a*, which are formed in turn of liquid impermeable sheets, the function of preventing the leakage of excreted fluids from the above-mentioned crotch part 21 when the above-mentioned diaper body 11 is worn can be improved further.

Furthermore, by providing the same arrangements as those of the respective embodiments described above, such as positioning third leg part elastic bodies 24 along flap parts 15 at the respective sides of diaper body 11 and between the vicinities of the positions at which first leg part elastic bodies 29 and the outer side parts of flap parts 15 at the respective sides of a main absorbent article body part 16 intersect and the vicinities of the positions at which second leg part elastic bodies 30 and the outer side parts of flap parts 15 at the respective sides of main absorbent article body part 16 intersect, etc., the same effects as the respective arrangements described above can be provided.

Figure 8:
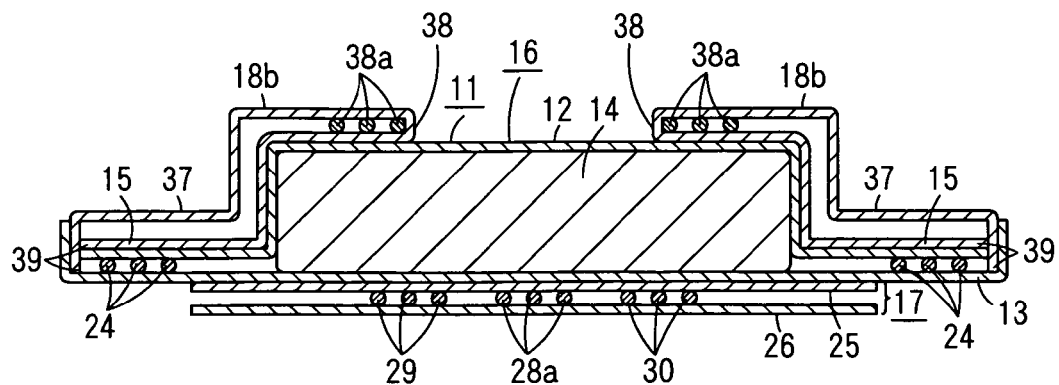
FIG. 8 is a front section of a disposable absorbent article of another embodiment of this invention.

Though the present embodiment is provided with an arrangement, wherein three-dimensional gather sheets 18*a*, forming parts of flap part 15 and three-dimensional gathers 37, are folded in two, base end parts 39 at one side are affixed and bonded by an adhesive agent, etc. to the vicinities of the respective width direction side parts of liquid permeable surface side sheet 12, and base end parts 39 at the other side are affixed and bonded by an adhesive agent, etc. to the vicinities of the respective width direction side parts of liquid impermeable back face side sheet 13, an arrangement is also possible wherein, as shown in FIG. 8, the positions of the respective width direction side parts of the above-mentioned liquid permeable surface side sheet 12 and the positions of the respective width direction side parts of the above-mentioned liquid impermeable back face side sheet 13 are made substantially the same, flap parts 15 are formed from the respective side parts of the above-mentioned liquid permeable surface side sheet 12 and the respective side parts of the above-mentioned liquid impermeable back face side sheet 13, and respective base end parts 39,39, formed by folding three-dimensional gather sheets 18*b*,18*b* that are in turn formed of a liquid impermeable sheet, are affixed to the respective outer edge parts of flap parts 15 to form three-dimensional gathers 37,37.

And since the positions of the respective width direction sides of the above-mentioned liquid permeable surface side sheet 12 and the positions of the respective width direction sides of the above-mentioned liquid impermeable back face side sheet 13 are made substantially the same and the respective base end parts 39,39, which are folded in two in the state in which the above-mentioned three-dimensional gather sheets 18b,18b and the respective base end parts 39,39 are substantially overlapped, can be positioned along the respective width direction side parts of the above-mentioned liquid permeable surface side sheet 12 and liquid impermeable back face side sheet 13, the above-mentioned three-dimensional gather sheets 18b,18b can be affixed and positioned readily with respect to the respective width direction side parts of the above-mentioned liquid permeable surface side sheet 12 and liquid impermeable back face side sheet 13, thus enabling the above-mentioned three-dimensional gathers 37 to be formed readily.

The arrangement of another embodiment of this invention's disposable absorbent article shall now be described with reference to FIG. 9. With regard to arrangements and actions that are the same as those of the embodiments described above, the same symbols shall be attached and description thereof shall be omitted.

Third leg part elastic bodies 24 are affixed in stretched states between the respective side parts of an above-mentioned liquid impermeable back face side sheet 13 and liquid impermeable sheets 18 at positions between the vicinities of the positions at which first leg part elastic bodies 29 and the outer side parts of flap parts 15 at the respective sides of a main absorbent article body part 16 intersect and the vicinities of the positions at which second leg part elastic bodies 30 and the outer side parts of flap parts 15 at the respective sides of main absorbent article body part 16 intersect.

These third leg part elastic bodies 24 are positioned at portions of leg parts 23 at the respective sides of an above-mentioned outer layer sheet 17 and parts thereof are positioned outward beyond leg parts 23 at the respective sides of the above-mentioned outer layer sheet 17.

At the vicinities of the positions at which the respective elastic bodies 29 and 30 intersect with flap parts 15, the above-mentioned third elastic bodies 24 intersect in the same plane with the other elastic bodies and the respective end parts thereof are positioned at the vicinities of these intersections. That is, third leg part elastic bodies 24 are positioned only in the central area in the longitudinal direction of an absorbent body 14. Put in another way, third leg part elastic bodies 24 are positioned across the vicinities of the positions at which the respective elastic bodies 29 and 30 intersect with the outer side parts of flap parts 15 at the respective sides of main absorbent article body part 16.

The actions of this embodiment shall now be described.

In being fitted on, diaper body 11 is fitted on readily like pants as with the respective embodiments described above.

Also by providing the same arrangements as those of the respective embodiments described above, such as positioning third leg part elastic bodies 24 along flap parts 15 at the respective sides of diaper body 11 and between the vicinities of the positions at which first leg part elastic bodies 29 and the outer side parts of flap parts 15 at the respective sides of main absorbent article body part 16 intersect and the vicinities of the positions at which second leg part elastic bodies 30 and the outer side parts of flap parts 15 at the respective sides of main absorbent article body part 16 intersect, etc., the same effects as the respective arrangements described above can be provided.

Of the respective side parts of main absorbent article body part 16, third leg part elastic bodies 24 are positioned only between the vicinities of the positions at which first leg part elastic bodies 29 and the outer side parts of flap parts 15 at the respective sides of main absorbent article body part 16 intersect and the vicinities of the positions at which second leg part elastic bodies 30 and the outer side parts of flap parts 15 at the respective sides of main absorbent article body part 16 intersect. Third leg part elastic bodies 24 are thereby positioned at just the locations, among the above-mentioned flap parts 15 at the respective sides of the above-mentioned main absorbent article body part 16, that are necessary for securing the function of putting crotch part 21 of the above-mentioned diaper body 11 in close contact with the crotch part of a wearer. As a result, the amount of elastic bodies used in third leg part elastic bodies 24 can be reduced and the manufacturing cost can be held down.

Figure 9:
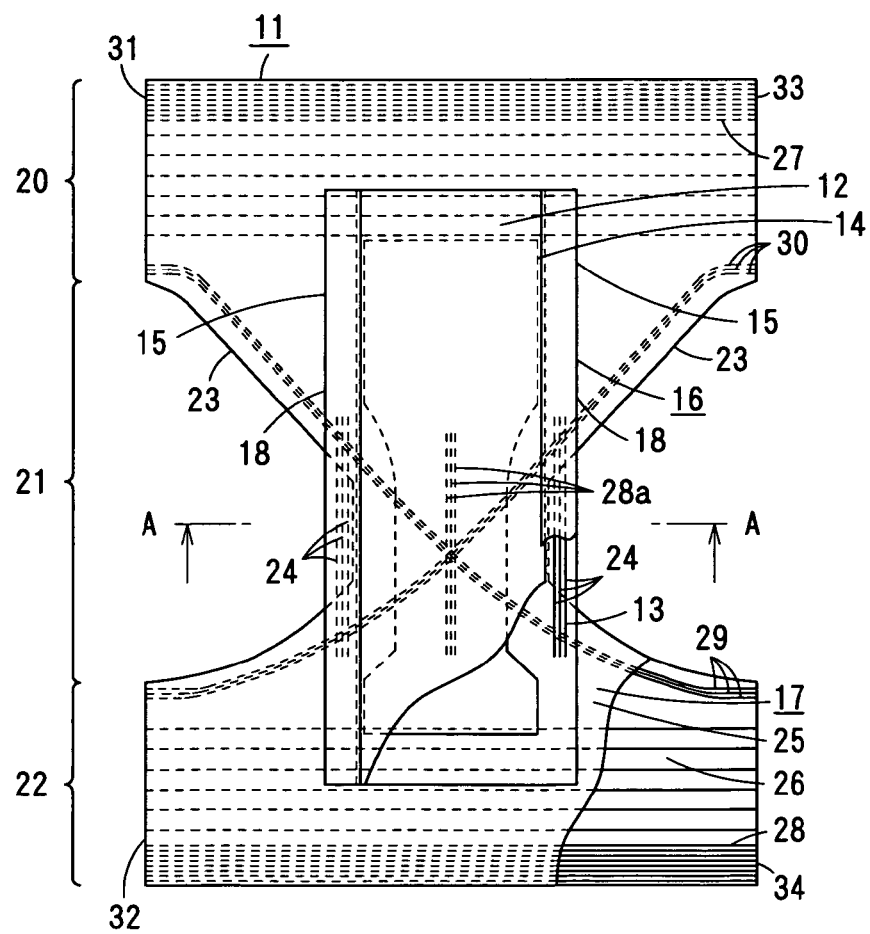
FIG. 9 is a partially cutaway plan view of a state in which a disposable absorbent article of another embodiment of this invention is spread out.
Figure 10:
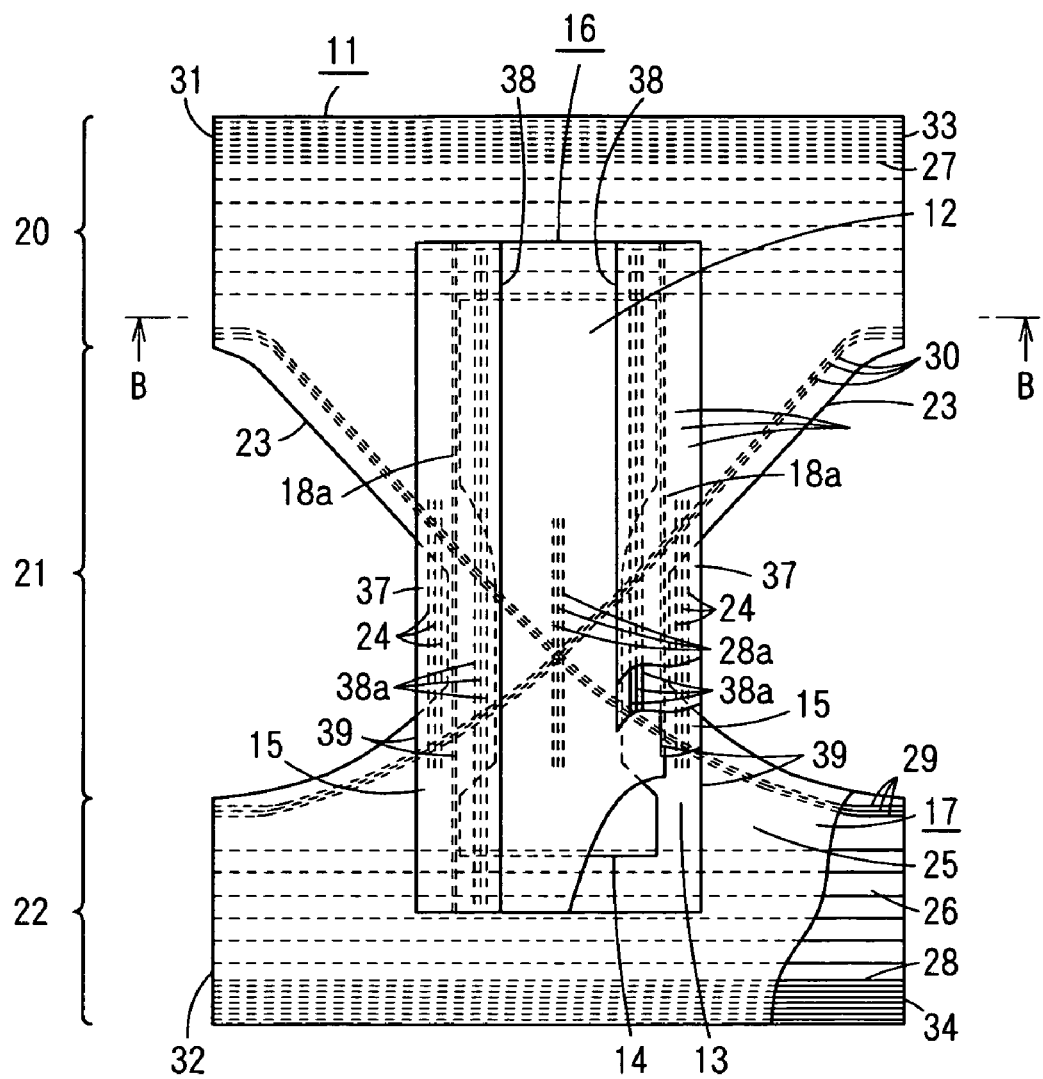
FIG. 10 is a front longitudinal section of a disposable absorbent article of another embodiment of this invention.

Though with this embodiment shown in FIG. 9, just flap parts 15 extend outward beyond the respective longitudinal direction end parts and the respective width direction side parts of the above-mentioned absorbent body 14 of diaper body 11 and third leg part elastic bodies 24 are positioned between the vicinities of the positions of the above-mentioned flap parts 15 at which first leg part elastic bodies 29 and the outer side parts of flap parts 15 at the respective sides of main absorbent article body part 16 intersect and the vicinities of the positions at which second leg part elastic bodies 30 and the outer side parts of flap parts 15 at the respective sides of main absorbent article body part 16 intersect, an arrangement may be provided instead wherein flap parts 15 are formed, as shown in FIG. 10, from parts of liquid permeable surface sheet 12 and liquid impermeable back face side sheet 13 that extend outward beyond the peripheral edges of the above-mentioned absorbent body 14 of diaper body 11 and three dimensional gather sheets 18a, which are layered and adhesively bonded to the above-mentioned liquid permeable surface side sheet 12 and the respective width direction side parts at the surface sides of the above-mentioned liquid impermeable back face side sheet 13, three-dimensional gathers 37,37 are formed from the above-mentioned three-dimensional gather sheets 18a at outer parts at the respective sides that are positioned outward in the width direction beyond the respective width direction side parts of the above-mentioned liquid impermeable back face side sheet 13, and third leg part elastic bodies 24 are positioned between the vicinities of positions of flap parts 15 at which first leg part elastic bodies 29 and the outer side parts of flap parts 15 at the respective sides of main absorbent article body part 16 intersect and the vicinities of the positions at which second leg part elastic bodies 30 and the outer side parts of flap parts 15 at the respective sides of main absorbent article body part 16 intersect.

Also with the above-described embodiment shown in FIG. 9 and the embodiment shown in FIG. 10, as long as third leg elastic bodies 24 have the respective end parts thereof positioned in the vicinities of the positions at which the respective elastic bodies 29 and 30 intersect with the outer side parts of flap parts 15 at the respective sides of main absorbent article body part 16, the same actions and effects are exhibited even if the respective end parts are positioned so as not to intersect with the respective elastic bodies 29 and 30, and in this case, the amount of elastic bodies used in third leg elastic bodies 24 can be reduced further and the manufacturing cost can be held down further.

Yet another embodiment of this invention's disposable absorbent article shall now be described with reference to FIG. 11. With regard to arrangements and actions that are the same as those of the embodiments described above, the same symbols shall be attached and description thereof shall be omitted.

Between an inner side sheet 25 and an outer side sheet 26 of an above-mentioned outer layer sheet 17, first leg part elastic bodies 29 have one end side set along a leg part 23 from a part of dorsal waist part 20 at one side, have an intermediate part 29b crossing an above-mentioned crotch part 21 straight along the width direction of the diaper body 11, that is, crossing the crotch part horizontally, and have the other end side set along the leg part 23 at a part of ventral waist part 22 at the other side.

Second leg part elastic bodies 30 have one end side set along a leg part 23 from a part of dorsal waist part 20 at the above-mentioned other side, have an intermediate part 30b crossing the above-mentioned crotch part 21 straight along the width direction of the diaper body 11, that is, crossing the crotch part horizontally, and have the other end side set along the leg part 23 at the above-mentioned one side of ventral waist part 22.

First leg part elastic bodies 29 and second leg part elastic bodies 30 have the respective intermediate parts 29b and 30b disposed in parallel to each other and at substantially equivalent positions at substantially the central region in the longitudinal direction of absorbent member 14 and are overlapped mutually across their entireties. That is, in the state in which diaper body 11 is spread out, intermediate parts 29b and 30b of the respective elastic bodies 29 and 30 are positioned in a substantially matched manner in plan view.

Also, third leg part elastic bodies 24 are respectively positioned at the vicinities of the positions at which the respective elastic bodies 29 and 30 intersect the outer side parts of flap parts 15 at the respective sides of main absorbent article body part 16 in a manner such that the respective end parts thereof are positioned between the positions of intersection.

Thus in comparison to the case where the first leg part elastic bodies and the second leg part elastic bodies are positioned in X-like form in diaper body 11 as a whole, first leg part elastic bodies 29 and second leg part elastic bodies 30 can be positioned close to the respective leg parts 23 to enable the respective leg parts 23 to be improved in stretchability, enable the respective elastic bodies 29 and 30 to be set along the leg parts of a wearer readily, and enable the respective elastic bodies 29, 30, and 24 to be positioned so as to surround substantially the entireties of leg parts 23 even when third leg part elastic bodies 24 are made short, thus enabling close contact with the leg parts of the wearer to be improved further and the function of preventing the leakage of excreted fluids from the respective leg parts 23 to be improved further.

Also in comparison to the case where the first leg part elastic bodies and the second leg part elastic bodies are positioned in X-like form in diaper body 11 as a whole, even when third leg part elastic bodies 24 are made short, the respective elastic bodies 29, 30, and 24 can be positioned so as to securely surround the respective leg parts 23 and third leg part elastic bodies 24 can be positioned readily, thereby enabling the manufacturing properties to be improved further, the usage amount of elastic bodies to be reduced, and the manufacturing cost to be held down.

Also, by substantially matching the respective intermediate parts of first leg part elastic bodies 29 and second leg part elastic bodies 30, the positioning of the respective elastic bodies 29 and 30 at the intermediate parts can be made left/right symmetric, and in comparison to the case where the intermediate parts are separated from each other, diaper body 11 can be prevented from becoming unwieldy and since the left and right sides stretch substantially equally, partial lowering of close contact, discomfort of a wearer, etc. due to imbalance of stretching in the left/right direction can be prevented as well.

Furthermore by providing the same arrangements as those of the respective embodiments described above, such as positioning third leg part elastic bodies 24 along flap parts 15 at the respective sides of diaper body 11 and between the vicinities of the positions at which first leg part elastic bodies 29 and the outer side parts of flap parts 15 at the respective sides of main absorbent article body part 16 intersect and the vicinities of the positions at which second leg part elastic bodies 30 and the outer side parts of flap parts 15 at the respective sides of main absorbent article body part 16 intersect, etc., the same effects as the respective arrangements described above can be provided.

With the above-described embodiment shown in FIG. 11, the state in which intermediate parts 29b and 30b of the respective elastic bodies 29 and 30 are substantially matched shall include states in which intermediate parts 29b and 30b are partially overlapped, states in which intermediate parts 29b and 30b are mutually adjacent in the longitudinal direction of diaper body 11, states in which the intermediate parts are slightly separated from each other in the longitudinal direction of diaper body 11, etc. as long as these states are within a range in which the stretching in the left/right direction of the respective elastic bodies 29,39 is balanced in a substantially symmetrical manner.

Also, though in the respective embodiments described above, diaper body 11 is formed to the pants form shown in FIG. 3, diaper body 11 may also be formed to the spread-out form of substantially rectangular shape that is long in the longitudinal direction as shown in FIG. 1. By forming diaper body 11 to the spread-out form, diaper body 11 can be fitted readily and securely even onto a wearer, such as a bed-ridden patient, who cannot put on diaper body 11 on his/her own.

This invention also includes an arrangement, wherein the intermediate parts, which are positioned in directions of crossing the above-mentioned crotch part 21, are positioned in states such that the intermediate parts will practically not stretch to a state in which the intermediate parts is less in tensile strength that the parts at one side and the other side of the above-mentioned first leg part elastic bodies 29 and second leg part elastic bodies 30 that are positioned along lag parts 23 at the respective sides.

An arrangement, wherein flap parts 15 as a whole do not protrude outward beyond leg parts 23 of outer layer sheet 17, that is, an arrangement wherein third leg part elastic members 24 are not positioned outward beyond outer layer sheet 17, is also possible.

INDUSTRIAL APPLICABILITY

As described above, this invention's disposable absorbent article can be used, for example, as a disposable diaper for adult use or for incontinence, etc.

The invention claimed is:

1. A disposable absorbent article comprising: a main absorbent article body part, in turn comprising a liquid permeable surface side sheet, a liquid impermeable back face side sheet, positioned at the back face side of the liquid permeable surface side sheet, an absorbent body, positioned between the liquid permeable surface side sheet and the liquid impermeable back face side sheet, and liquid impermeable flap parts, the flap parts being disposed at least at the peripheral edge parts of said liquid impermeable back face side sheet and extending outward beyond the respective sides in the width direction of said absorbent body; and an outer layer sheet, positioned at the back face side of the liquid impermeable back face side sheet of the main absorbent article body part; and wherein a dorsal waist part, a crotch part, having leg parts at both sides, and a ventral waist part are formed successively and integrally in the longitudinal direction, a dorsal waist part elastic body and a ventral waist part elastic body of said outer layer sheet, which stretch in the width direction of the outer layer sheet, are disposed respectively at the dorsal waist part and the ventral waist part of said outer layer sheet, leg part elastic bodies are disposed respectively at said leg parts at the respective sides of said outer layer sheet, central elastic bodies are affixed to the outer layer sheet at the crotch part positioned along the longitudinal direction of the absorbent body substantially centered in the width direction of the absorbent body;

said leg part elastic bodies are formed as first leg part elastic bodies and second leg part elastic bodies, said first leg part elastic bodies have one end side set along a leg part from a part of said dorsal waist part at one side, have an intermediate part crossing said crotch part obliquely towards a part of said ventral waist part at the other side, and have the other end side set along the leg part at the part of said ventral waist part at the other side, said second leg part elastic bodies have one end side set along a leg part from a part of said dorsal waist part at the other side, have an intermediate part intersecting said first leg part elastic bodies and crossing said crotch part obliquely towards a part of said ventral waist part at the one side, and have the other end side set along the leg part at the part of said ventral waist part side at the one side, and third leg part elastic bodies are disposed between the liquid impermeable flap parts and the liquid impermeable back face side sheet at both sides of said main absorbent article body part, wherein the first, second and third leg part elastic plastic bodies intersect with each other five times, wherein the third leg part elastic bodies extend in a longitudinal direction beyond the points of intersection with the first leg part elastic bodies and the second leg part elastic bodies at the respective sides of the main absorbent article body part, the third leg part elastic bodies extend in a longitudinal direction substantially the length of the main absorbent article body part; one end of the third leg part elastic bodies in the longitudinal direction is at least disposed in the vicinity of the dorsal waist part elastic body, the opposite end of the third leg part elastic bodies in the longitudinal direction is at least disposed in the vicinity of the ventral waist part elastic body; and one lateral side of the absorbent body substantially perpendicular to the longitudinal direction is at least disposed in the vicinity of the dorsal waist part elastic body, while the opposite lateral side of the absorbent body is at least disposed in the vicinity of the ventral waist part elastic body.

2. A disposable absorbent article comprising: a main absorbent article body part having a longitudinal axis and a lateral axis perpendicular thereto, the main absorbent article body part in turn comprising a liquid permeable surface side sheet, a liquid impermeable back face side sheet, positioned at the back face side of the liquid permeable surface side sheet, an absorbent body, positioned between the liquid permeable surface side sheet and the liquid impermeable back face side sheet, and liquid impermeable flap parts, the flap parts being disposed at least at the peripheral edge parts of said liquid impermeable back face side sheet and extending outward beyond the respective sides in the width direction of said absorbent body; and an outer layer sheet, positioned at the back face side of the liquid impermeable back face side sheet of the main absorbent article body part; and wherein a dorsal waist part, a crotch part, having leg parts at both sides, and a ventral waist part are formed successively and integrally in the longitudinal direction, a dorsal waist part elastic body and a ventral waist part elastic body, which stretch in the width direction of the outer layer sheet, are disposed respectively at the dorsal waist part and the ventral waist part of said outer layer sheet, leg part elastic bodies are disposed respectively at said leg parts at the respective sides of said outer layer sheet, central elastic bodies are affixed to the outer layer sheet at the crotch part positioned along the longitudinal direction of the absorbent body substantially centered in the width direction of the absorbent body;

said leg part elastic bodies are formed as first leg part elastic bodies and second leg part elastic bodies, said first leg part elastic bodies have one end side set along a leg part from a part of said dorsal waist part at one side, have an intermediate part extending across said crotch part along the width direction, and have the other end side set along the leg part at a part of the ventral waist part at the other side, said second leg part elastic bodies have one end side set along a leg part from a part of said dorsal waist part at the other side, have an intermediate part substantially mirroring the intermediate part of said first leg part elastic bodies relative to the longitudinal axis and crossing said crotch part in a direction substantially parallel to the lateral axis, and have the other end side set along the leg part at a part of said ventral waist part side at the one side, and third leg part elastic bodies are disposed between the liquid impermeable flap parts and the liquid impermeable back face side sheet at both sides of said main absorbent article body part, wherein the third leg part elastic bodies extend in a longitudinal direction beyond the points of intersection with the first leg part elastic bodies and the second leg part elastic bodies at the respective sides of the main absorbent article body part, the third leg part elastic bodies extend in a longitudinal direction substantially the length of the main absorbent article body part; one end of the third leg part elastic bodies in the longitudinal direction is at least disposed in the vicinity of the dorsal waist part elastic body, the opposite end of the third leg part elastic bodies in the longitudinal direction is at least disposed in the vicinity of the ventral waist part elastic body; and one lateral side of the absorbent body substantially perpendicular to the longitudinal direction is at least disposed in the vicinity of the dorsal waist part elastic body, while the opposite lateral side of the absorbent body is at least disposed in the vicinity of the ventral waist part elastic body.

3. The disposable absorbent article according to claim 1, wherein the main absorbent article body part is affixed to the outer layer sheet at the back face side, the crotch part of the outer layer sheet is notched so as to be substantially concave towards the inner sides in the width direction, and the third leg part elastic bodies, which are positioned at the flap parts of said main absorbent body part, have at least a portion thereof disposed along the central lateral axis X-X outward beyond the leg parts at the respective sides of the outer layer sheet.

4. The disposable absorbent article according to claim 1, wherein the third leg part elastic bodies are positioned at least respectively between the vicinities of the positions at which the first leg part elastic bodies and the outer side parts of the flap parts at the respective sides of the main absorbent article body part intersect and the vicinities of the positions at which the second leg part elastic bodies and the outer side parts of the flap parts at the respective sides of the main absorbent article body part intersect.

5. The disposable absorbent article according to claim 1, wherein a pair of three-dimensional gathers, which are erected in the direction of the body of a wearer when the absorbent article body is fitted onto the body of the wearer, are formed in mutually opposing manner at outer side parts at the respective sides that are positioned outwards in the width direction beyond the vicinities of the third leg part elastic bodies of the main absorbent article body part.

6. The disposable absorbent article according to claim 1, wherein each of the first leg part elastic bodies and second leg part elastic bodies is arranged to be lower in tensile strength at the intermediate part, positioned in the direction of crossing said crotch part, than at the one end side and the other end side that are positioned along the leg parts at the respective sides.

7. The disposable absorbent article according to claim 2, wherein the main absorbent article body part is affixed to the outer layer sheet at the back face side, the crotch part of the outer layer sheet is notched so as to be substantially concave towards the inner sides in the width direction, and the third leg part elastic bodies, which are positioned at the flap parts of said main absorbent body part, have at least a portion thereof disposed along the central lateral axis X-X outward beyond the leg parts at the respective sides of the outer layer sheet.

8. The disposable absorbent article according to claim 2, wherein the third leg part elastic bodies are positioned at least respectively between the vicinities of the positions at which the first leg part elastic bodies and the outer side parts of the flap parts at the respective sides of the main absorbent article body part intersect and the vicinities of the positions at which the second leg part elastic bodies and the outer side parts of the flap parts at the respective sides of the main absorbent article body part intersect.

9. The disposable absorbent article according to claim 2, wherein a pair of three-dimensional gathers, which are erected in the direction of the body of a wearer when the absorbent article body is fitted onto the body of the wearer, are formed in mutually opposing manner at outer side parts at the respective sides that are positioned outwards in the width direction beyond the vicinities of the third leg part elastic bodies of the main absorbent article body part.

10. The disposable absorbent article according to claim 2, wherein each of the first leg part elastic bodies and second leg part elastic bodies is arranged to be lower in tensile strength at the intermediate part, positioned in the direction of crossing said crotch part, than at the one end side and the other end side that are positioned along the leg parts at the respective sides.

11. The disposable absorbent article according to claim 1, wherein the flap part is an impervious sheet.

12. The disposable absorbent article according to claim 2, wherein the flap part is an impervious sheet.

13. The disposable article according to claim 1, wherein the outer layer sheet is formed by overlapping a liquid impermeable inner sheet piece and a liquid impermeable outer sheet piece; and the central elastic bodies, the first leg part elastic bodies and the second leg part elastic bodies are disposed between the inner sheet piece and the outer sheet piece.

14. The disposable article according to claim 2, wherein the outer layer sheet is formed by overlapping a liquid impermeable inner sheet piece and a liquid impermeable outer sheet piece; and the central elastic bodies, the first leg part elastic bodies and the second leg part elastic bodies are disposed between the inner sheet piece and the outer sheet piece.

* * * * *